(12) United States Patent
Thomas

(10) Patent No.: US 10,506,408 B2
(45) Date of Patent: Dec. 10, 2019

(54) METHOD, APPARATUS AND COMPUTER-READABLE MEDIUM FOR AIDING EMERGENCY RESPONSE

(71) Applicant: Bryx, Inc., Rochester, NY (US)

(72) Inventor: David Thomas, Rochester, NY (US)

(73) Assignee: Bryx, Inc., Rochester, NY (US)

( * ) Notice: Subject to any disclaimer, the term of this patent is extended or adjusted under 35 U.S.C. 154(b) by 0 days.

(21) Appl. No.: 15/498,889

(22) Filed: Apr. 27, 2017

(65) Prior Publication Data

US 2017/0318448 A1    Nov. 2, 2017

Related U.S. Application Data

(60) Provisional application No. 62/328,348, filed on Apr. 27, 2016, provisional application No. 62/432,167, filed on Dec. 9, 2016.

(51) Int. Cl.

| | |
|---|---|
| *H04W 4/90* | (2018.01) |
| *G16H 40/20* | (2018.01) |
| *G06F 19/00* | (2018.01) |
| *G08B 25/10* | (2006.01) |
| *H04W 4/02* | (2018.01) |
| *H04M 1/725* | (2006.01) |

(52) U.S. Cl.
CPC .......... *H04W 4/90* (2018.02); *G06F 19/3418* (2013.01); *G08B 25/10* (2013.01); *G16H 40/20* (2018.01); *H04M 1/72538* (2013.01); *H04W 4/023* (2013.01)

(58) Field of Classification Search
CPC . G08B 7/066; G06F 19/3418; G06F 19/3406; G06F 19/322; G06F 17/30247; G06Q 50/24; H04W 4/90

USPC .......... 340/521; 705/2, 3; 600/407; 370/260
See application file for complete search history.

(56) References Cited

U.S. PATENT DOCUMENTS

| | | | | |
|---|---|---|---|---|
| 7,261,691 | B1 * | 8/2007 | Asomani | A61B 5/1112 128/920 |
| 7,263,379 | B1 * | 8/2007 | Parkulo | G08B 21/02 340/501 |
| 7,602,277 | B1 * | 10/2009 | Daly | G08B 27/005 340/438 |

(Continued)

FOREIGN PATENT DOCUMENTS

CA        2928197 A1     4/2015

OTHER PUBLICATIONS

International Search Report and Written Opinion of the International Searching Authority completed Aug. 14, 2017.

*Primary Examiner* — Hoi C Lau
(74) *Attorney, Agent, or Firm* — Timothy W. Menasco, Esq.; Harter Secrest & Emery LLP

(57) ABSTRACT

Presented is a method, apparatus, and computer-readable medium for aiding emergency response. An exemplary method includes receiving, by a processor, a first data, the first data related to medical information of an individual, and receiving, by a processor, a plurality of second data, the plurality of second data from a plurality of devices with information of the individual. The method further includes determining, by the processor, a trauma level of the individual based on the received first data and the received plurality of second data, and transmitting, by the processor, the first data and the plurality of second data to a trauma center.

20 Claims, 18 Drawing Sheets

(56) References Cited

U.S. PATENT DOCUMENTS

| | | | | |
|---|---|---|---|---|
| 7,720,458 B2* | 5/2010 | Impson | H04L 12/66 | 340/539.13 |
| 7,761,309 B2* | 7/2010 | Sacco | G06F 19/3481 | 705/2 |
| 7,860,583 B2* | 12/2010 | Condurso | G06F 19/326 | 700/2 |
| 7,907,053 B2* | 3/2011 | Wildman | G01S 5/02 | 340/539.1 |
| 8,441,356 B1* | 5/2013 | Tedesco | G08B 21/0453 | 340/539.15 |
| 8,576,066 B2* | 11/2013 | Bivens | G08B 25/003 | 340/539.13 |
| 8,734,340 B2* | 5/2014 | Shibata | A61B 5/0002 | 600/300 |
| 9,035,744 B2* | 5/2015 | Waniss | H04M 1/72527 | 340/5.1 |
| 9,300,799 B2* | 3/2016 | Brown | H04M 3/5116 | |
| 2002/0004729 A1* | 1/2002 | Zak | G16H 10/60 | 705/3 |
| 2002/0097159 A1* | 7/2002 | Hooglander | G06K 7/0021 | 340/573.1 |
| 2002/0103622 A1* | 8/2002 | Burge | G07C 5/008 | 702/183 |
| 2003/0212575 A1* | 11/2003 | Saalsaa | G06Q 10/10 | 705/2 |
| 2003/0234725 A1* | 12/2003 | Lemelson | G08B 7/066 | 340/521 |
| 2004/0078227 A1* | 4/2004 | Morris | G06F 19/322 | 705/2 |
| 2004/0100376 A1* | 5/2004 | Lye | A61B 5/411 | 340/539.12 |
| 2004/0246128 A1* | 12/2004 | Menard | A61B 5/0002 | 340/539.19 |
| 2006/0017560 A1* | 1/2006 | Albert | G08B 1/08 | 340/531 |
| 2006/0069326 A1* | 3/2006 | Heath | A61H 31/005 | 601/41 |
| 2009/0182426 A1* | 7/2009 | Von Arx | A61B 5/0031 | 623/11.11 |
| 2009/0222539 A1* | 9/2009 | Lewis | G06F 19/322 | 709/221 |
| 2010/0001838 A1* | 1/2010 | Miodownik | G06Q 10/06 | 340/10.1 |
| 2010/0102123 A1* | 4/2010 | Skowronek | G06Q 20/20 | 235/380 |
| 2011/0060378 A1* | 3/2011 | Tuysserkani | A61N 1/39 | 607/5 |
| 2011/0099031 A1* | 4/2011 | Nair | G06F 19/3418 | 705/3 |
| 2011/0117878 A1* | 5/2011 | Barash | H04W 4/90 | 455/404.2 |
| 2011/0295078 A1* | 12/2011 | Reid | G06F 19/3406 | 600/300 |
| 2012/0191476 A1* | 7/2012 | Reid | G06Q 50/24 | 705/3 |
| 2012/0319836 A1* | 12/2012 | Reeder | A61B 5/0002 | 340/539.12 |
| 2013/0035581 A1* | 2/2013 | Vesto | G06F 19/322 | 600/407 |
| 2013/0096649 A1* | 4/2013 | Martin | G06F 19/322 | 607/60 |
| 2013/0246960 A1* | 9/2013 | Saylors | G06F 19/3406 | 715/771 |
| 2014/0184408 A1* | 7/2014 | Herbst | G08B 25/016 | 340/539.12 |
| 2014/0294257 A1* | 10/2014 | Tussy | G06F 17/30247 | 382/118 |
| 2015/0036551 A1* | 2/2015 | Pappas | H04W 4/22 | 370/260 |
| 2015/0095053 A1* | 4/2015 | Amann | A61B 5/04012 | 705/2 |
| 2015/0100326 A1* | 4/2015 | Kowalkiewicz | G06Q 10/06 | 705/2 |
| 2015/0100348 A1* | 4/2015 | Connery | G06Q 50/24 | 705/3 |
| 2015/0269826 A1* | 9/2015 | Zhang | G08B 21/0446 | 340/539.12 |
| 2015/0339913 A1* | 11/2015 | Lyman | H04W 4/90 | 340/287 |
| 2016/0093197 A1* | 3/2016 | See | G08B 25/016 | 340/539.12 |
| 2016/0232304 A1* | 8/2016 | Goyal | G06Q 50/22 | |
| 2017/0007129 A1* | 1/2017 | Kaib | A61B 5/0022 | |
| 2017/0053086 A1* | 2/2017 | Martin | G06F 19/3418 | |
| 2017/0068785 A1* | 3/2017 | Experton | G06F 19/322 | |
| 2017/0108342 A1* | 4/2017 | Foreman | G01C 21/3691 | |
| 2017/0161438 A1* | 6/2017 | Connery | G06F 19/322 | |
| 2017/0287315 A1* | 10/2017 | Kaur | H04W 4/90 | |
| 2017/0293988 A1* | 10/2017 | Goyal | G06Q 50/24 | |
| 2017/0296107 A1* | 10/2017 | Reid | A61B 5/1171 | |
| 2017/0318448 A1* | 11/2017 | Thomas | G16H 40/20 | |
| 2017/0325091 A1* | 11/2017 | Freeman | H04W 12/06 | |
| 2018/0000346 A1* | 1/2018 | Cronin | A61B 5/6898 | |
| 2018/0004909 A1* | 1/2018 | Cronin | G06F 19/00 | |
| 2018/0181714 A1* | 6/2018 | Pillarisetty | G16H 50/30 | |

* cited by examiner

1702: (a) receiving, by a processor, a first data, the first data related to medical information of an individual; (b) receiving, by a processor, a plurality of second data, the plurality of second data from a plurality of devices with information of the individual; (c) determining, by the processor, a trauma level of the individual based on the received first data and the received plurality of second data; and(d) transmitting, by the processor, the first data and the plurality of second data to a trauma center

1704: the method further comprising sending an alert with the first data and the plurality of second data to a trauma center

1706: wherein the first data includes medical information from a first responder.

1708: wherein the second data includes medical information from at least one of a heart rate monitor, a blood pressure measuring device, an automobile OBD, an IV, an oxygen level measuring device, and a thermometer

1710: wherein the trauma center is a set of trauma center personnel able to respond to the trauma level

1712: wherein the trauma center is a hospital

1714: wherein the transmitting includes an alert and an estimated time of arrival

1716: wherein determining a trauma level includes determining a medical treatment for the individual

FIG. 17

1802: (a) receiving, by a processor, a first data, the first data related to medical information of an individual; (b) receiving, by a processor, a plurality of second data, the plurality of second data from a plurality of devices with medical information of the individual; (c) determining, by the processor, (i) a profile based on the first data and the plurality of second data, and (ii) which subset of a plurality of user equipments require the profile, and (d) transmitting, by the processor, the profile to the subset of the plurality of user equipments.

1804: wherein the determining which subset of the plurality of user equipments require the profile is based on a location of the individual and an expertise of the user of the subset of the plurality of the user equipments

1806: wherein a trauma center to which the individual will be transported is part of the subset of the plurality of user equipments

1808: wherein the first data comprises at least one of injury information, heart rate, blood pressure, an oxygen level, and temperature

1810: wherein the second data includes medical information from at least one of a heart rate monitor, a blood pressure measuring device, an automobile OBD, an IV, an oxygen level measuring device, and a thermometer

1812: wherein the transmitting includes an alert and an estimated time of arrival

FIG. 18

METHOD, APPARATUS AND COMPUTER-READABLE MEDIUM FOR AIDING EMERGENCY RESPONSE

BACKGROUND OF THE INVENTION

Field of the Invention

Exemplary embodiments of the present disclosure relate to an emergency information system. Exemplary embodiments of the present disclosure relate more particularly to an emergency response system with a method, apparatus, and computer-readable medium.

Description of Related Art

An emergency room or casualty department is a medical facility specializing in emergency medicine and the acute care of patients who arrive without a prior appointment either by their own means or by that of an ambulance. The emergency department is typically a department of a hospital or other primary care center.

Due to the unplanned nature of patient attendance, the department must provide initial treatment for a broad spectrum of illnesses and injuries, some of which may be life-threatening and require immediate attention. In some countries, emergency departments have become important entry points for those without other means of access to medical care. The emergency department of most hospitals operate 24 hours a day, although staffing levels may be varied in an attempt to reflect patient volume.

SUMMARY OF THE INVENTION

In view of the foregoing, it is an object of the present disclosure to provides a method, apparatus and computer-readable medium for aiding emergency response.

A first exemplary embodiment of the present disclosure provides a method for aiding emergency response. The method includes receiving, by a processor, a first data, the first data related to medical information of an individual, and receiving, by a processor, a plurality of second data, the plurality of second data from a plurality of devices with information of the individual. The method further including determining, by the processor, a trauma level of the individual based on the received first data and the received plurality of second data, and transmitting, by the processor, the first data and the plurality of second data to a trauma center.

A second exemplary embodiment of the present disclosure provides an apparatus for aiding emergency response. The apparatus includes at least one processor and a memory storing computer program instructions executable by the at least one processor, wherein the memory and the computer program instructions and the processor are configured to cause the apparatus to at least receive a first data, the first data related to medical information of an individual. The apparatus with the memory and the computer program instructions and the processor are configured to cause the apparatus to with the receive a plurality of second data, the plurality of second data from a plurality of devices with information of the individual, and determine a trauma level of the individual based on the received first data and the received plurality of second data, and transmit the first data and the plurality of second data to a trauma center.

A third exemplary embodiment of the present disclosure provides a computer-readable medium for aiding emergency response. The non-transitory computer-readable medium tangibly storing computer program instructions which when executed by a processor, cause the processor to at least receive a first data, the first data related to medical information of an individual, and receive a plurality of second data, the plurality of second data from a plurality of devices with information of the individual. The non-transitory computer-readable medium tangibly storing computer program instructions which when executed by a processor further cause the processor to determine a trauma level of the individual based on the received first data and the received plurality of second data, and transmit the first data and the plurality of second data to a trauma center.

A fourth exemplary embodiment of the present disclosure provides a method for aiding emergency response. The method includes receiving, by a processor, a first data, the first data related to medical information of an individual, and receiving, by a processor, a plurality of second data, the plurality of second data from a plurality of devices with medical information of the individual. The method further including determining, by the processor, (i) a profile based on the first data and the plurality of second data, and (ii) which user equipments require the profile, and transmitting, by the processor, the profile to the user equipments.

A fifth exemplary embodiment of the present disclosure provides an apparatus for aiding emergency response. The apparatus includes at least one processor and a memory storing computer program instructions executable by the at least one processor, wherein the memory and the computer program instructions and the processor are configured to cause the apparatus to at least receive a first data, the first data related to medical information of an individual. The memory and the computer program instructions and the processor are further configured to cause the apparatus to receive a plurality of second data, the plurality of second data from a plurality of devices with information of the individual, and determine determining, by the processor, (i) a profile based on the first data and the plurality of second data, and (ii) which user equipments require the profile, and transmitting, by the processor, the profile to the user equipments.

A sixth exemplary embodiment of the present disclosure provides a non-transitory computer-readable medium for aiding emergency response. The non-transitory computer-readable medium tangibly storing computer program instructions which when executed by a processor, cause the processor to at least receive a first data, the first data related to medical information of an individual. The non-transitory computer-readable medium tangibly storing computer program instructions which when executed by a processor further cause the processor to receive a plurality of second data, the plurality of second data from a plurality of devices with information of the individual, and determine determining, by the processor, (i) a profile based on the first data and the plurality of second data, and (ii) which user equipments require the profile, and transmitting, by the processor, the profile to the user equipments.

The following will describe embodiments of the present disclosure, but it should be appreciated that the present disclosure is not limited to the described embodiments and various modifications of the invention are possible without departing from the basic principle. The scope of the present disclosure is therefore to be determined solely by the appended claims.

BRIEF DESCRIPTION OF THE SEVERAL VIEWS OF THE DRAWING(S)

FIG. 17 is a logic flow diagram suitable for preforming exemplary embodiments of the present disclosure.

FIG. 18 is another logic flow diagram suitable for preforming exemplary embodiments of the present disclosure.

DETAILED DESCRIPTION OF THE INVENTION

Following or during an emergency situation (e.g., fire, car accident, or medical emergency) emergency responders or first responders (e.g., police, fire fighters, or EMTs) will arrive at the location of the emergency situation. If individuals involved in the emergency situation are injured or require medical attention, the first responders will typically take the individuals to a local hospital. During the ambulance ride to the hospital as well as during their assessment at the emergency location, the first responders will gather data or information regarding the cause of the emergency, their effects on the individuals involved, as well as possible treatments.

For instance, an EMT may arrive at the scene of a car accident wherein one of the drivers has sustained a head injury. The EMT may assess the cause of the accident, the point of contact, whether the driver was wearing a seat belt, and the injuries sustained by the driver. If needed, the EMT may take the driver to a local hospital emergency room. During or prior to the drive to the hospital, the EMT may illicit the driver's medical history and take the driver's vital signs (e.g., blood pressure, heart rate, loss of blood). The EMT may also administer fluids into the injured driver through an IV. The EMT and other first responders at the emergency location will thus have information related to the injured driver's medical condition that will be valuable in making a determination of the proper care required upon arrival to the hospital. However, current emergency response systems are not operable to convey all of the pertinent information available in treating individuals that arrive to a hospital emergency room. Additionally, current emergency response systems fail to provide advanced notice to the hospital emergency room of incoming patients as well as their medical conditions such that the emergency rooms and their staff are properly prepared at the time the patient arrives.

Embodiments of the present disclosure provide a method, apparatus, and computer-readable medium for providing enhanced emergency information to hospital personnel. Embodiments of the present disclosure provide hospitals including emergency rooms with alerts indicating the expected arrival time of an incoming patient, the known medical needs and medical history of the incoming patient, and in some instances the patient's (or ambulance, car, truck, helicopter, or bus transporting the patient) GPS coordinates. Embodiments of the present disclosure provide first responders with the ability to alert hospital staff of incoming patients. Embodiments of the present disclosure provide hospital staff with incoming patient vital signs and other medical data prior to the patient's arrival.

Figure 1:
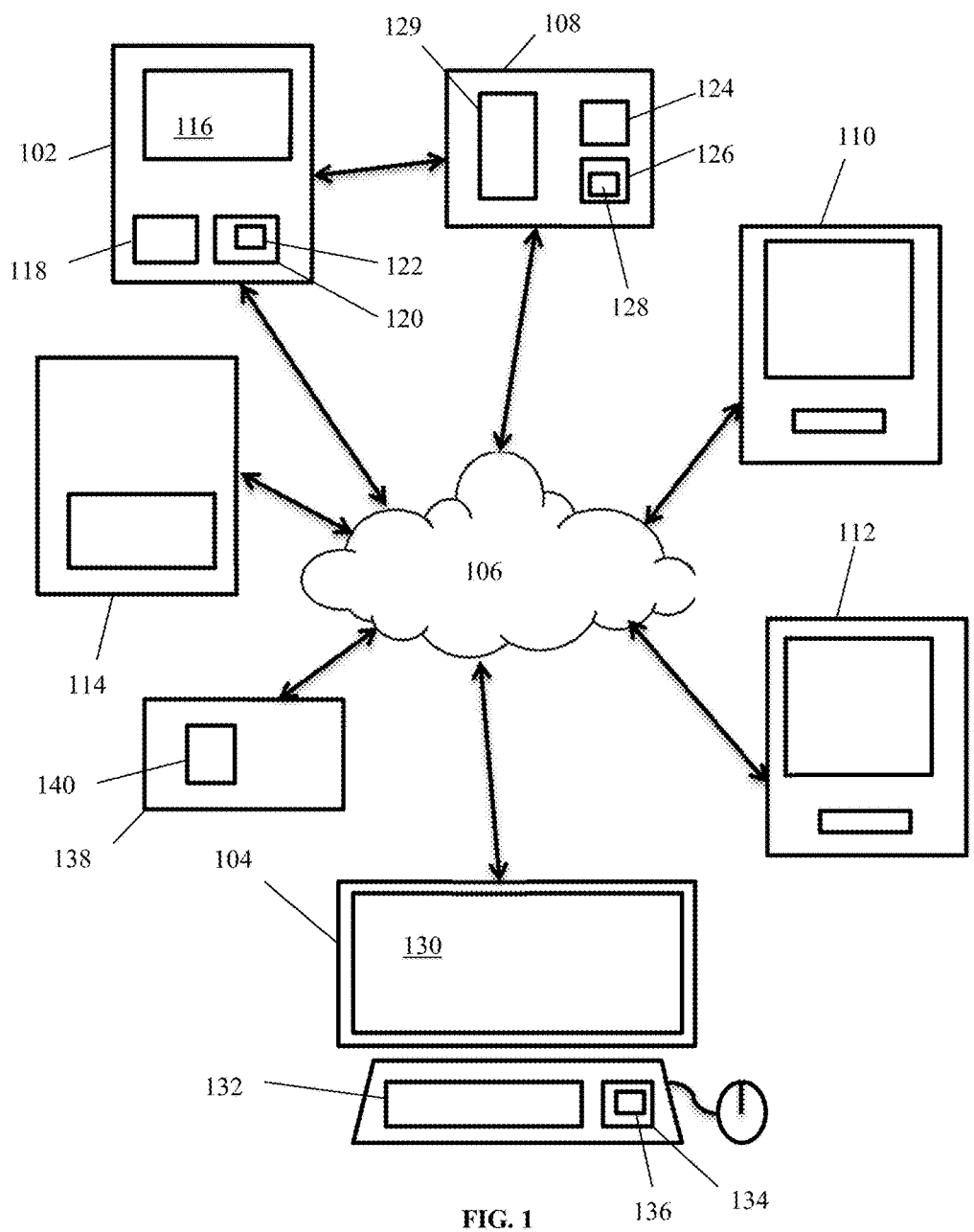
FIG. 1 is an exemplary signaling diagram between devices suitable for performing exemplary embodiments of the present disclosure.

Referring to FIG. 1, shown is an exemplary signaling diagram suitable for performing exemplary embodiments of the present disclosure. Shown in FIG. 1 is emergency responder user equipment (UE) 102, 911 dispatch 108, server 106, trauma center 104, medical device 114, vehicle (e.g., automobile) 138, and trauma center user equipments 110, 112. Emergency responder UE 102 and trauma center user equipments 110, 112 can include any type of electronic device operable to perform the functions described herein. Examples of emergency responder UE 102 include smartphones, cell phones, tablets, laptop computers, wearable devices and the like. Embodiments of emergency responder UE 102 include at least a processor 118, a memory 120 storing computer program instructions 122, a user interface 116 which may include a display and the ability to transmit and receive data (either via wired or wireless connections) with server 106 or directly with any of the other elements depicted in FIG. 1. While trauma center user equipments 110, 112 do not depict all of the elements of emergency responder UE 102, it should be appreciated that embodiments of trauma center user equipments 110 and 112 include all of the elements of emergency responder user equipment UE 102. Embodiments of emergency responder UE 102 are operable to allow a user to enter patient medical information into an application running on emergency responder UE 102 and then transmit the patient medical information.

911 dispatch 108 includes any type of 911 call center known in the art. 911 dispatch 108 can also include a user interface 129 (which may include a display), a processor 124, a memory 126 storing computer program instructions 128, and the ability to transmit and receive data (either via wired or wireless connections) with other elements depicted in FIG. 1. 911 dispatch 108 can be operable such that medical, accident, or emergency information relayed to the 911 dispatcher can be entered manually or automatically (e.g., through voice recognition software) and transmitted to other elements depicted in FIG. 1.

Server 106 is operable to communicate with the other elements depicted in FIG. 1. Server 106 can include public and private servers and can include at least one processor, at least one memory storing computer program instructions. In one embodiment, server 106 includes the internet. Trauma center 104 can include one or more computers, user equipments, laptops, digital displays, tablets, smartphones, wearables and the like. Embodiments of trauma center 104 include at least one processor 132, at least one memory 134 storing computer program instructions 136, a user interface 130 (which may include a display), and a transmitter and a receiver. Trauma center 104 is operable to communicate with other elements depicted in FIG. 1.

In practice, emergency medical services (EMS) would receive a 911 call regarding an emergency situation at 911 dispatch 108. The EMS will be dispatched to the scene of the emergency and will assess and triage the patient. This can include determining the nature of the medical emergency (e.g., car injuries, smoke inhalation, burns from a fire, heart attack, etc.) and possible on sight treatment. The EMS will then enter the medical information into an application on a mobile device such as emergency responder user equipment 102. An exemplary mobile device includes a mobile phone, smart phone, tablet, laptop computer, wearable device and the like. For instance, if the patient has suffered a heart attack the EMS may enter the heart rate, blood pressure and oxygen levels of the patient into the mobile device. The application will then determine a trauma level for the patient. The trauma level will be a numerical indicator of the seriousness of the medical emergency as it relates to the patient. For instance, level 1 may indicate life threatening medical emergencies, such as gunshots or stroke victims, while higher numbered levels indicate less threatening medical emergencies, such as a broken arm or concussion.

Figure 2:
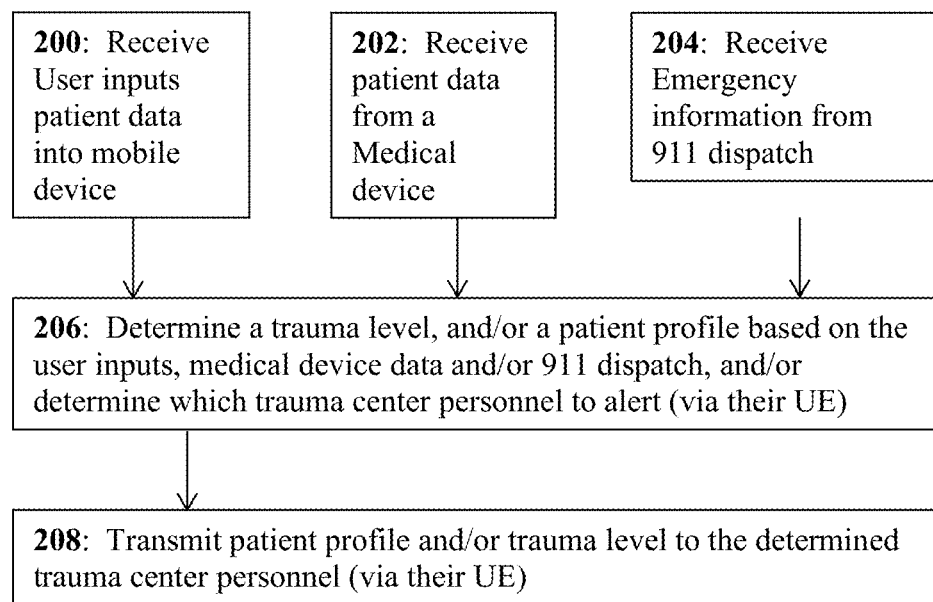
FIG. 2 is an exemplary logic flow diagram suitable for performing exemplary embodiments of the present disclosure.

Referring to FIG. 2, shown is a simplified logic flow diagram illustrating an exemplary process for performing exemplary embodiments of the present disclosure. At block 200, receive (e.g., by a server, UE or trauma center) user (e.g., first responder, EMS, emergency responder) inputs patient data into a mobile device (e.g., emergency responder UE 102). The patient data will relate to medical information of a patient or individual that is involved in an emergency or accident. At block 202, receive (e.g., by a server, UE or trauma center) patient data from a medical device (e.g., blood pressure device, heart rate monitor, etc.). At block 204, receive (e.g., by a server, UE or trauma center) emergency information from 911 dispatch. At block 206, determine (e.g., by a server, UE or trauma center) a trauma level, and/or a patient profile based on the user inputs, medical device data and/or 911 dispatch, and determine which trauma center personnel to alert (via their UE). Then at block 208, transmit patient profile and/or trauma level to the determined trauma center personnel (via their UE).

Embodiments of the present disclosure provide that the EMS mobile device or application is operable to automatically determine what the types of medical expertise (including doctors with certain medical specialties) are required to address the medical situation of the patient. For instance, the application is operable to determine whether adult medical care as opposed to pediatric care is required based on the age of the patient. Also, for example, the application is operable to determine whether a cardiologist vs. a neurologist is required based on the symptoms of the patient.

Embodiments of the present disclosure provide that the first responder may take certain medical measurements with medical device 114. Embodiments provide that medical device 114 can automatically transmit medical information to an emergency responder UE 102, a server 106 or to a hospital or trauma center 104. For instance, a heart rate monitor may be attached to a patient in an ambulance on route to a hospital. Embodiments provide that the heart rate monitor can automatically upload/transmit the heart rate information to the emergency responder user equipment 102 or server 106 so that it can be sent to the hospital staff via trauma center UEs 110, 112. Other medical instruments including IVs, thermometers, oxygen level measuring devices, blood pressure measuring devices, and the like are similarly operable. The medical information can be transmitted from the medical devices through wired, wireless, or Bluetooth connection to the mobile device.

Figure 3:
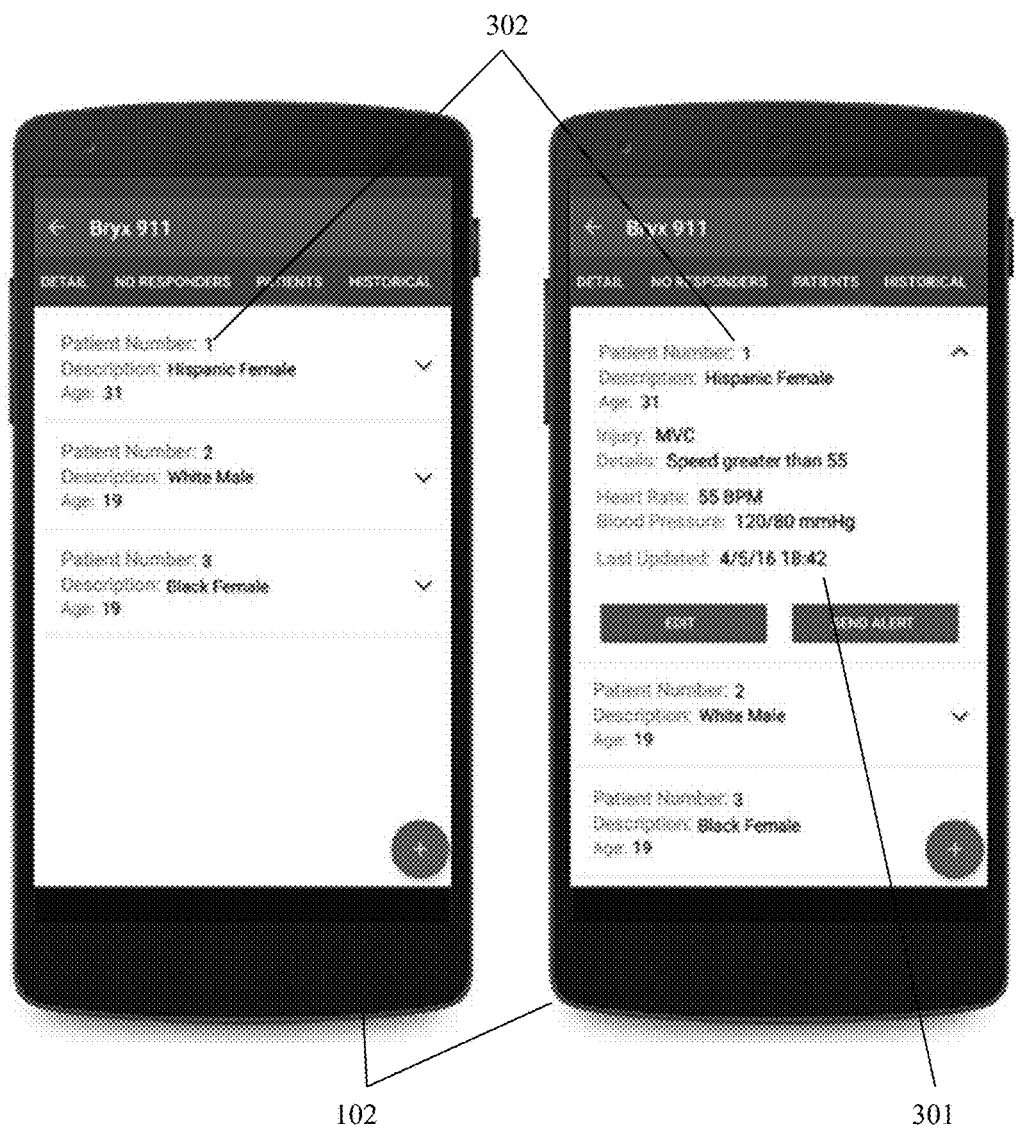
FIG. 3 illustrates some of the exemplary information available in embodiments of an application of the present disclosure.

In another embodiment, medical information input into emergency responder UE 102 and medical information from medical device 114 is received (e.g., by emergency responder UE 102, server 106, or trauma center 104) and used to determine (1) a patient profile 301, and (2) which trauma center personnel should be notified with the profile. The profile can include a summary of the relevant patient medical information inputted by the emergency response on the emergency responder UE 102 and from medical device 114 and/or 911 dispatch 108. Embodiments of a profile are depicted in FIG. 3, FIG. 4, FIG. 6, FIG. 9, FIG. 10, and FIG. 11, which illustrates UE 302 having some of the exemplary patient information available in an exemplary profile. As shown in FIG. 3, FIG. 4, FIG. 6, FIG. 9, FIG. 10, and FIG. 11, some of the information available in a profile includes a patient number (e.g., a unique identifier), a description of the patient, age, injury, details of how the injury was acquired, heart rate, blood pressure, and the date and time that the profile was last updated. Also shown in FIG. 3 is that embodiments provide that a UE can maintain more than one patient profile. A user can select which patient profile to view in order to view more detailed information. The profile can also include a geographic location of the patient with a map as well as directions or an estimated time of arrival to a the location of the patient or to some other location (e.g., a trauma center).

In one embodiment, a particular patient can be assigned a unique identifier 302 (shown in FIG. 3), which can be linked to all of the medical information inputted by EMS into the EMS mobile device or application and the medical information received from medical devices to the particular patient. As shown in FIG. 3 is UE 102 operable to perform exemplary embodiments of the present disclosure. An exemplary unique identifier 302 can include a barcode, a number, a 3D barcode, and the like. For instance, if EMS are responding to an emergency situation involving 100 or more injured individuals, it is often difficult for EMS and hospitals to keep track of the number of injured persons, the types of injuries and the location of each individual. Embodiments provide that each individual can be assigned a barcode, which is linked to that particular individuals medical information. The barcode for each individual may be transmitted with each of the individual's medical information. Embodiments further provide that EMS personnel and hospital staff will be able to obtain a particular individual's medical information by inputting the unique identifier of the individual into the mobile device or application. In the instance the unique identifier is a barcode, scanning (e.g., by a mobile device or other device operable to read a barcode) the barcode associated with an individual will retrieve the known medical information of the individual. Embodiments also provide that a hospital or trauma center will be able to view the number of individuals involved in an emergency incident by tracking the number of unique identifiers. For example, all of the unique identifiers can be sent to the hospital or trauma center and displayed along with their location and types of injuries, such that the hospital can track the total number of incoming or existing patients.

Embodiments further provide that the location of individuals can be tracked by the location of the unique identifier. In one embodiment, each unique identifier will be scanned by EMS personnel when the particular individual is moved such that EMS personnel and hospitals to which they are going will be able to track the location of the individual. In another embodiment, each individual will be associated with a personal GPS (e.g., a smartphone or GPS device) that is linked to the unique identifier such that movement of the individual will be able to be tracked through the application and by EMS and hospital personnel.

The application, through the mobile device, will then transmit the entered patient information (via wired or wireless communication) to the hospital or other trauma center to which the patient is going to be transported. The application will alert the hospital or other trauma center with the known medical information (which can include a unique identifier associated with the patient) as well as an estimated time of arrival. The notification to the hospital can be through a mobile device or devices or a central system maintained by the hospital to track and triage current patients.

Upon receipt of the notification from the EMS mobile device, the hospital staff will be able to review the emergency situation as it relates to the incoming patient and determine what medical staff is required to treat the patient. For instance, if the patient is suffering from a brain injury, the hospital staff may want to notify an on call neurosurgeon that the patient will be arriving shortly. Embodiments further provide that hospital staff or trauma personnel who receive the notification will be able to acknowledge the alert such that the EMS that sent the alert will be notified that their alert was received. Upon acknowledgement, embodiments of the application will operably send an alert (e.g., through "SEND ALERT" button 304 shown in FIG. 3 or "ALERT" button 602 shown in FIG. 6) to on-call staff at the hospital or trauma center notifying the on-call staff of the known medical information and the ETA of the patient. In yet another embodiment, if hospital staff or trauma personnel fail to acknowledge the alert, the alert will automatically be sent to the on-call staff, which will be able to acknowledge the alert through an application on their mobile device. In another embodiment, if the on-call staff fails to acknowledge the alert, the application will automatically cycle through different appropriate (based on ability to respond to the type of emergency or injury) on-call staff until an acknowledgement is received. In a further embodiment, EMS may be able to call directly the on-call staff if no acknowledgement is received.

Embodiments of the present disclosure provide that based on the information provided to the application, the application will be able to transmit a message alerting (shown in FIG. 3, FIG. 6, FIG. 7) a particular set of hospital staff that a patient will be arriving soon with a specific set of injuries (including injuries from severe trauma to basic non-life threatening injuries). For instance, if EMS identifies that the patient is a victim of a gunshot wound to the chest, the application will automatically transmit an alert to the hospital staff that has expertise with gunshot victims with the medical information of the patient and their ETA to the hospital.

In another instance, EMS may identify the patient as a woman going into premature labor. In this instance, the application will transmit an alert to the hospital OBGYN and an anesthesiologist with the medical information of the patient and their ETA to the hospital.

It should be appreciated that information transmitted by the application from any device (including a mobile device used by EMS, a medical device for taking a patient's vital signs, or other similar device) can transmit the medical information to a central server. The server will then transmit the relevant information or all of the information to the appropriate hospital, trauma center, or individual. In another embodiment, the application or mobile device will transmit the medical information directly to the appropriate hospital, trauma center, or individual.

Figure 6:
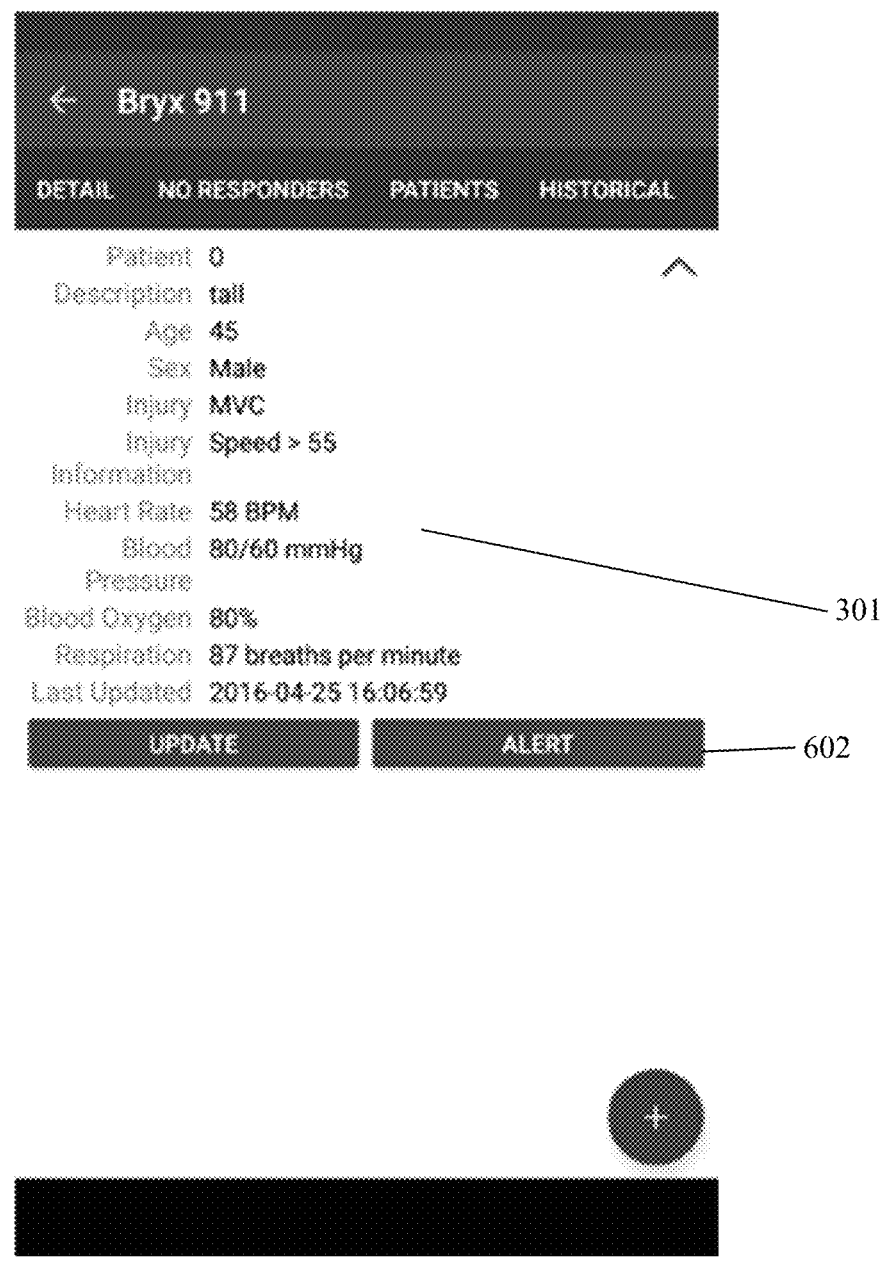
FIG. 6 is an exemplary display of patient information suitable for performing exemplary embodiments of the present disclosure.
Figure 7:
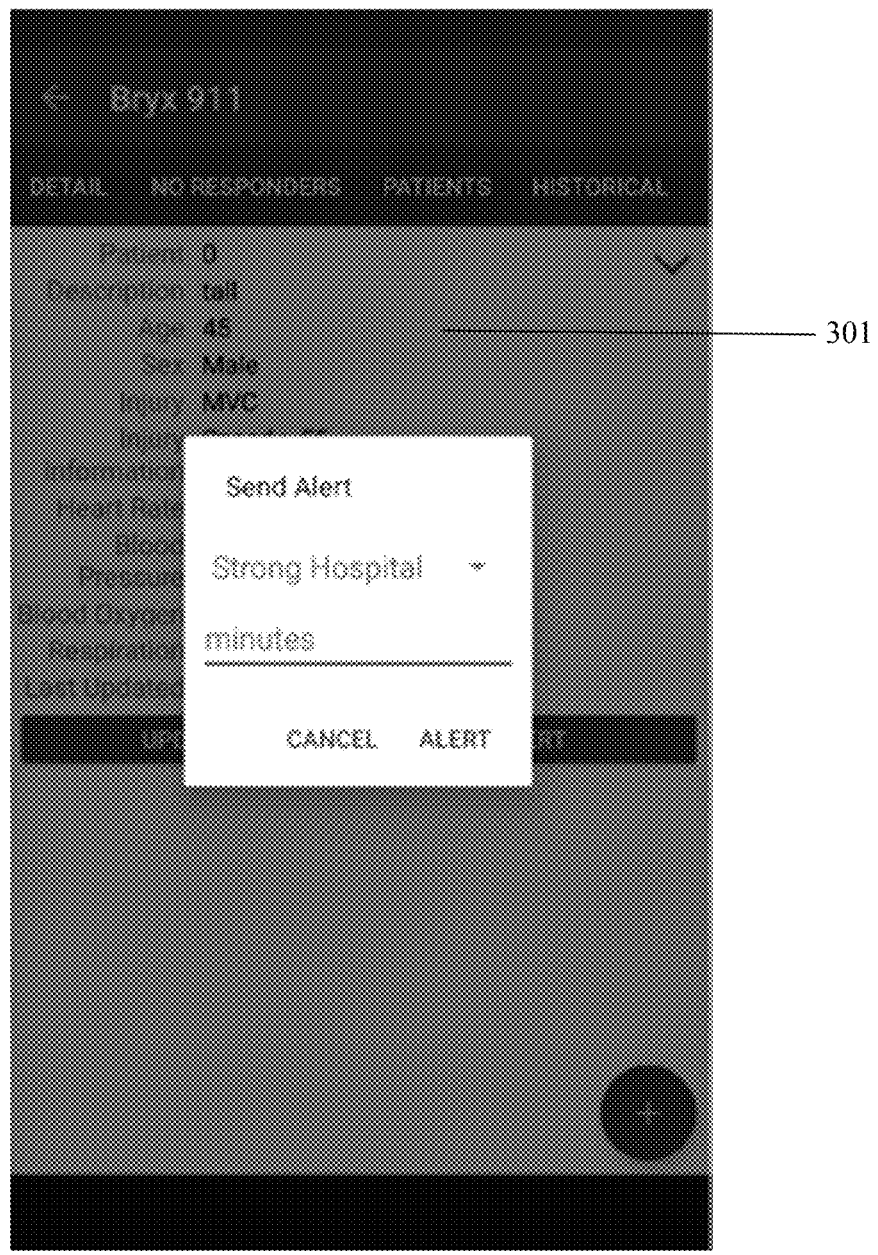
FIG. 7 illustrates an exemplary alert suitable for performing exemplary embodiments of the present disclosure.
Figure 8:
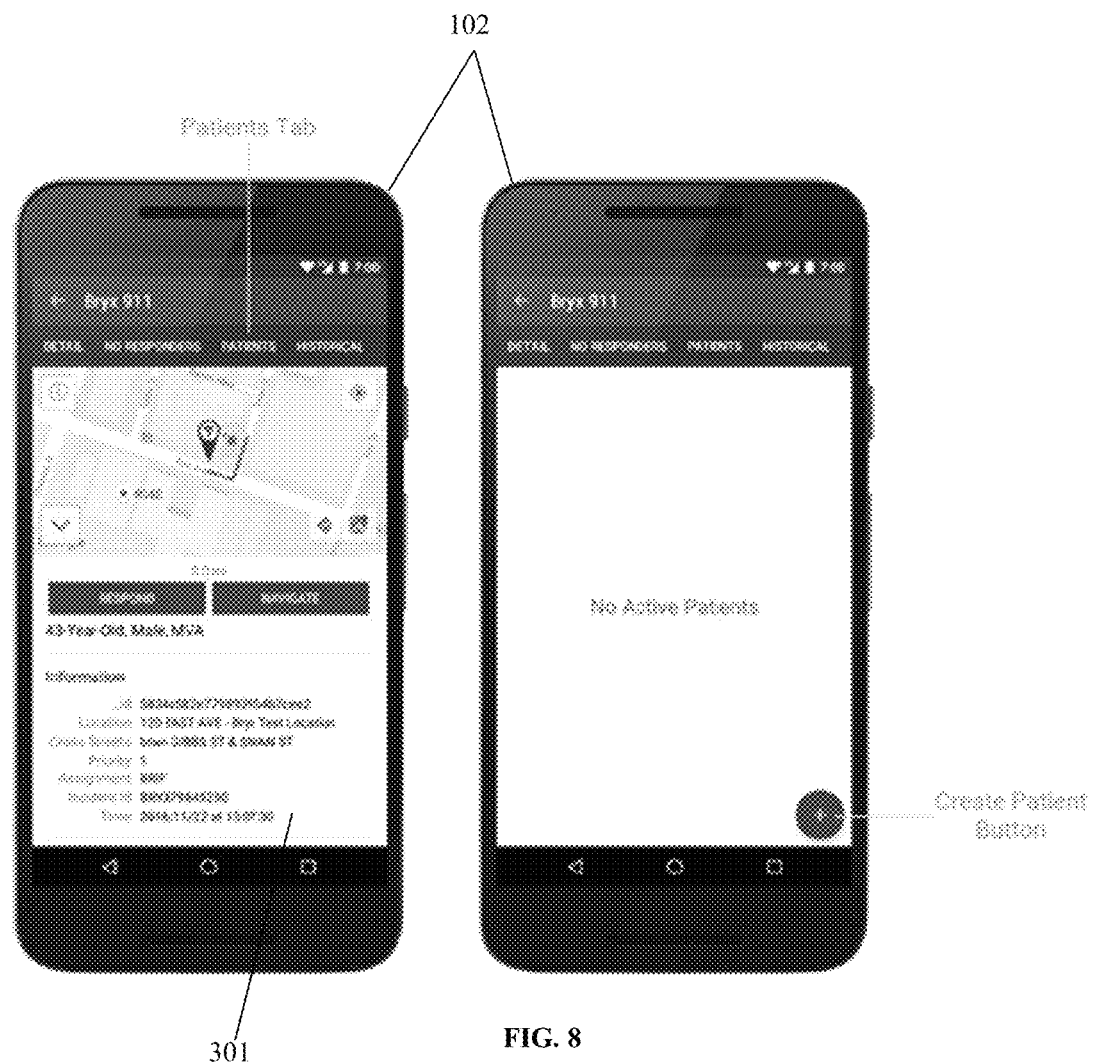
FIG. 8 illustrates exemplary patient injury information suitable for performing exemplary embodiments of the present disclosure.
Figure 8A:
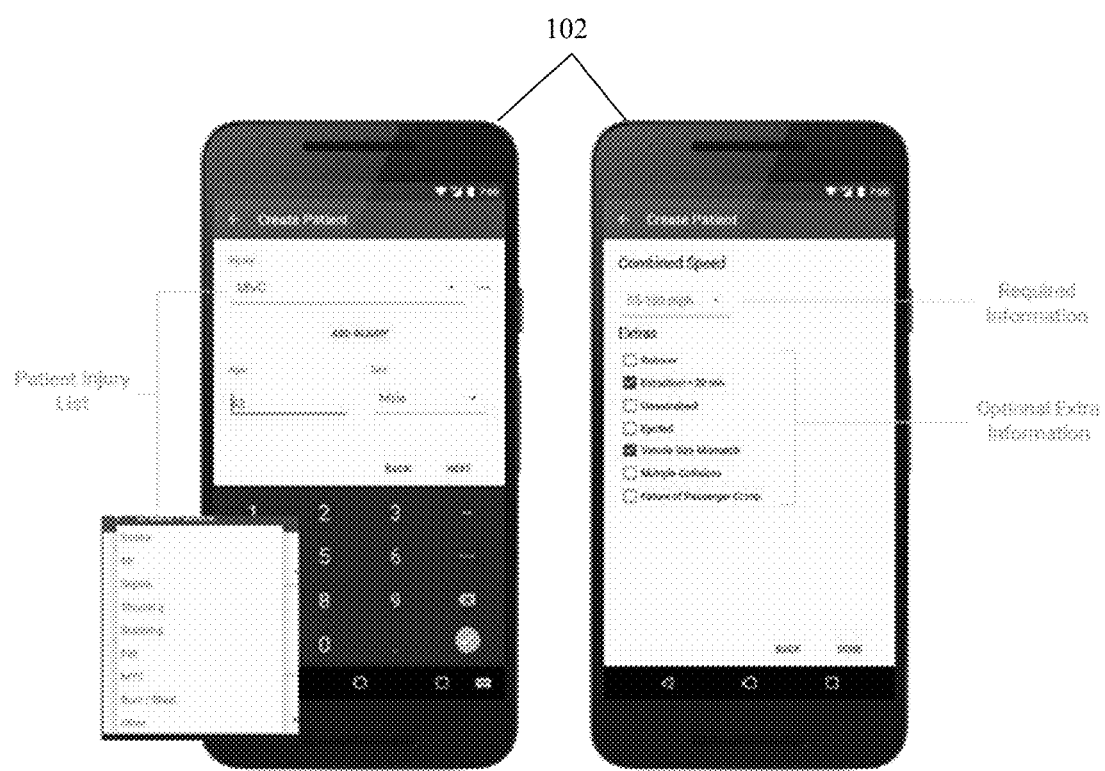
FIG. 8a illustrates exemplary patient injury information suitable for performing exemplary embodiments of the present disclosure.
Figure 9:
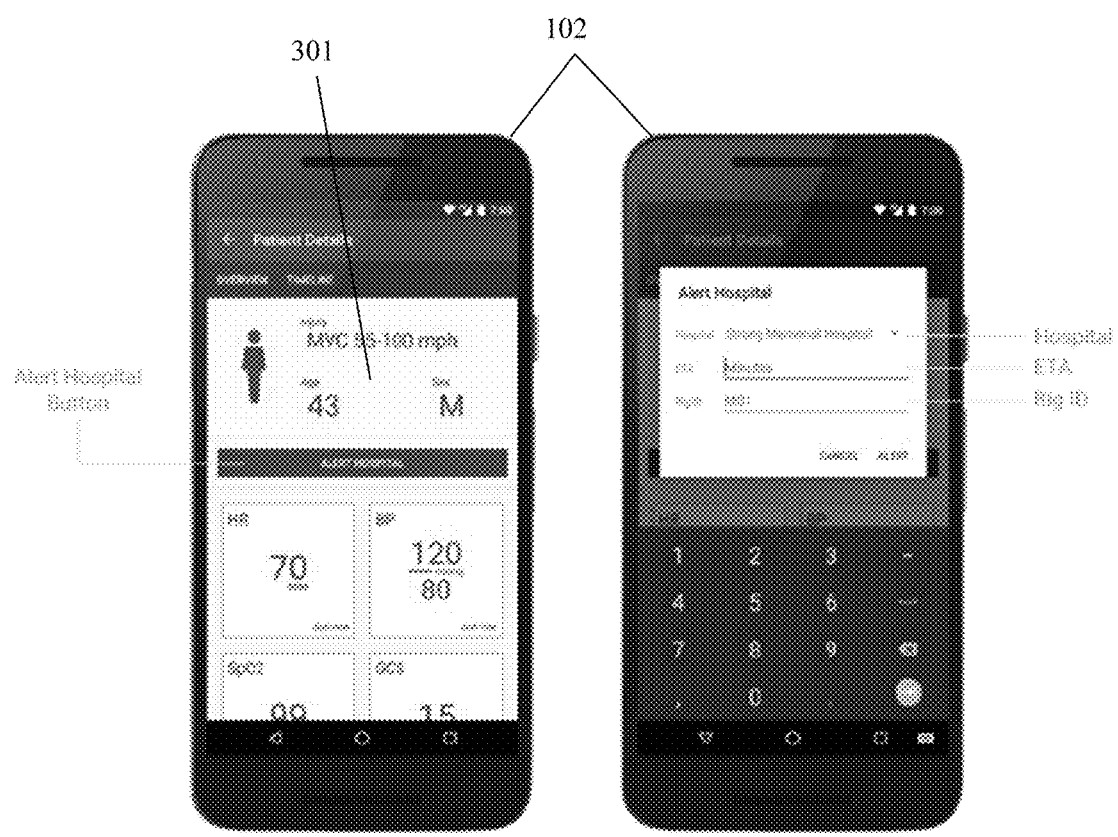
FIG. 9 illustrates an exemplary alert suitable for performing exemplary embodiments of the present disclosure.
Figure 10:
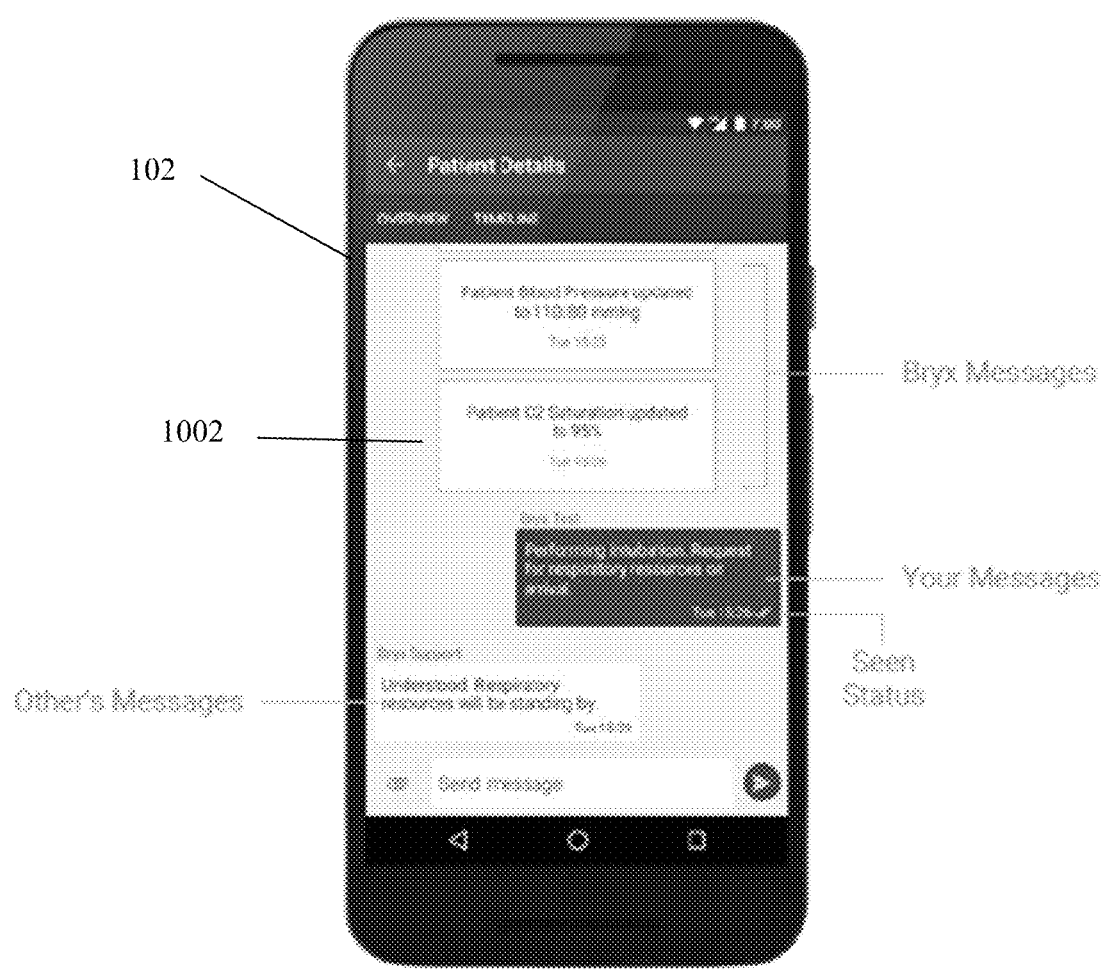
FIG. 10 illustrates an exemplary patient timeline suitable for performing exemplary embodiments of the present disclosure.
Figure 11:
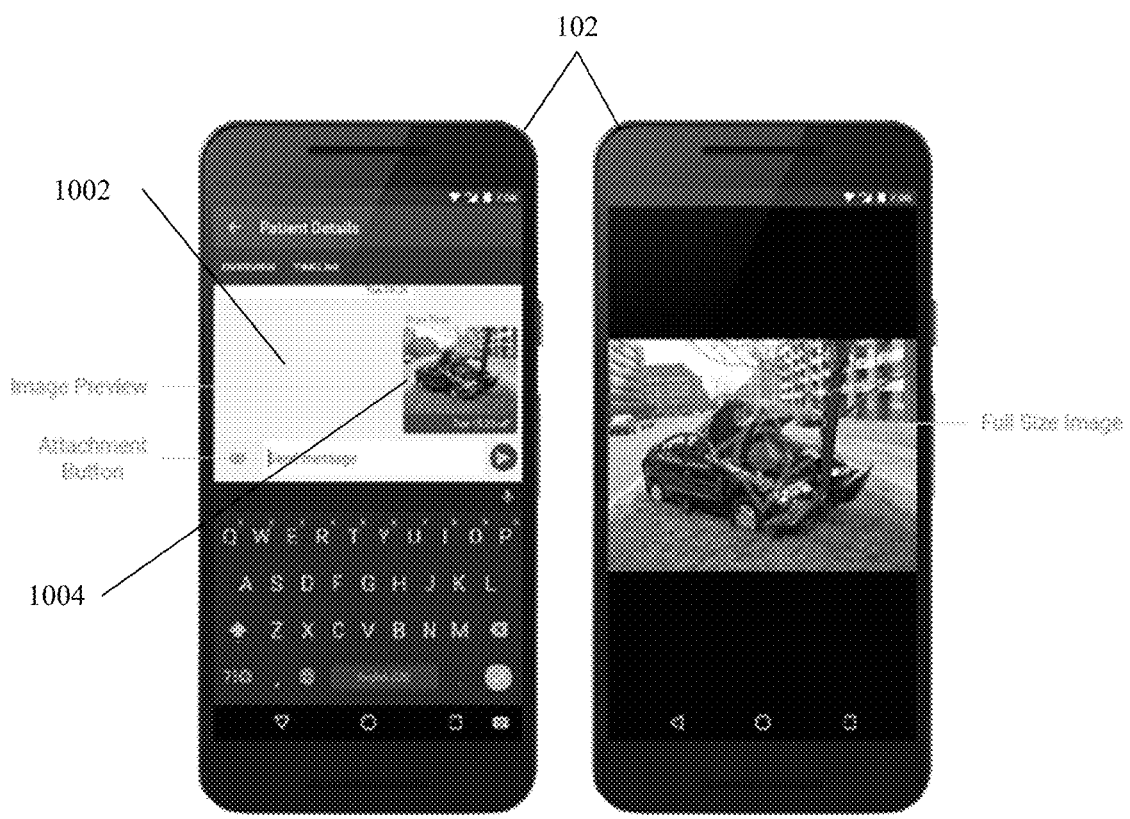
FIG. 11 illustrates exemplary image messaging suitable for performing exemplary embodiments of the present disclosure.
Figure 12:
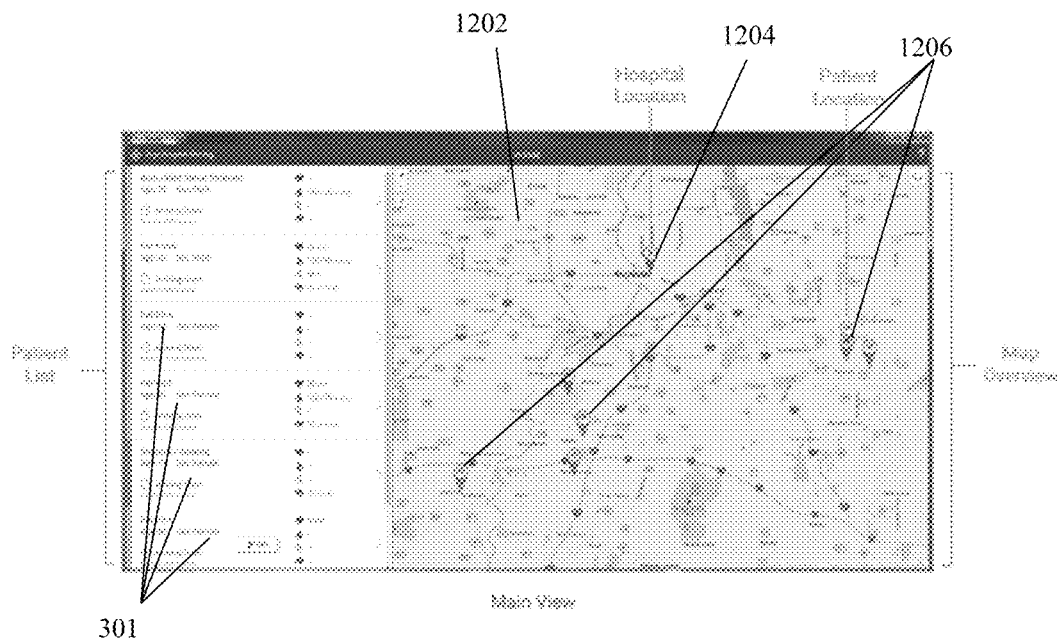
FIG. 12 is an exemplary map with a plurality of patient profiles suitable for performing exemplary embodiments of the present disclosure.
Figure 13:
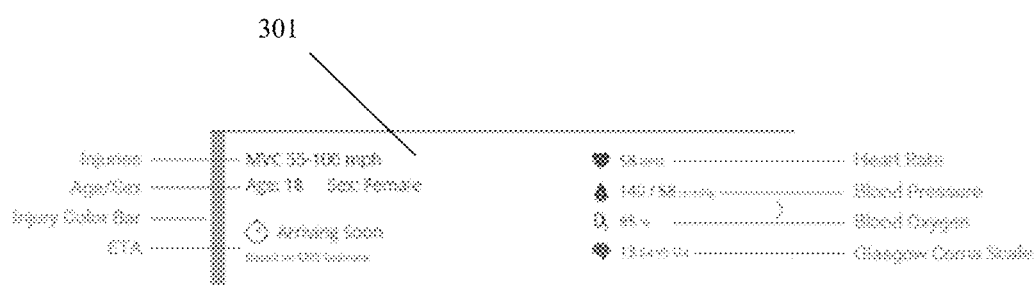
FIG. 13 is a close-up view of a portion of an exemplary patient profile suitable for performing exemplary embodiments of the present disclosure.
Figure 14:
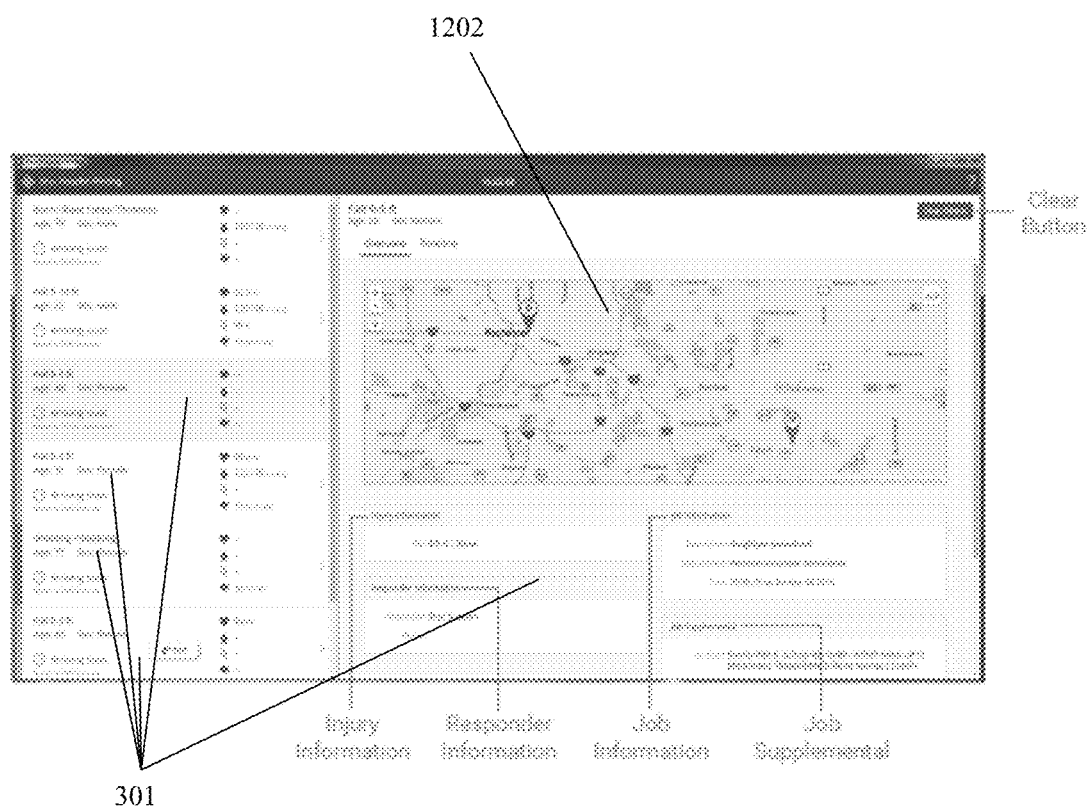
FIG. 14 is another exemplary map with a plurality of patient profiles suitable for performing exemplary embodiments of the present disclosure.
Figure 15:
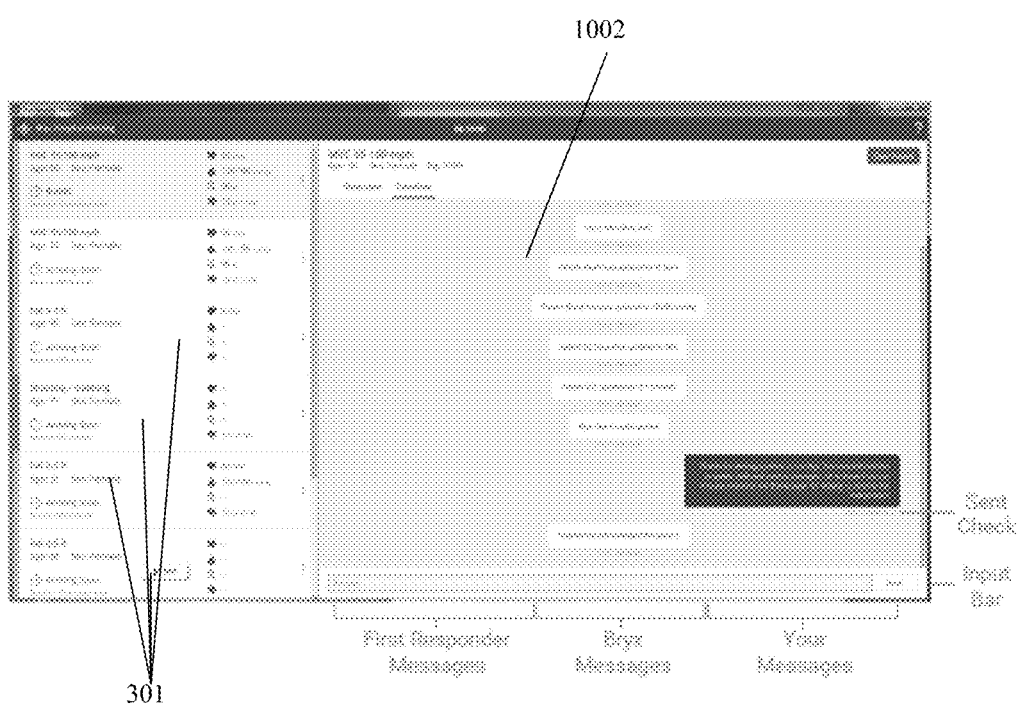
FIG. 15 is an exemplary patient timeline with a plurality of patient profiles suitable for performing exemplary embodiments of the present disclosure.
Figure 16:
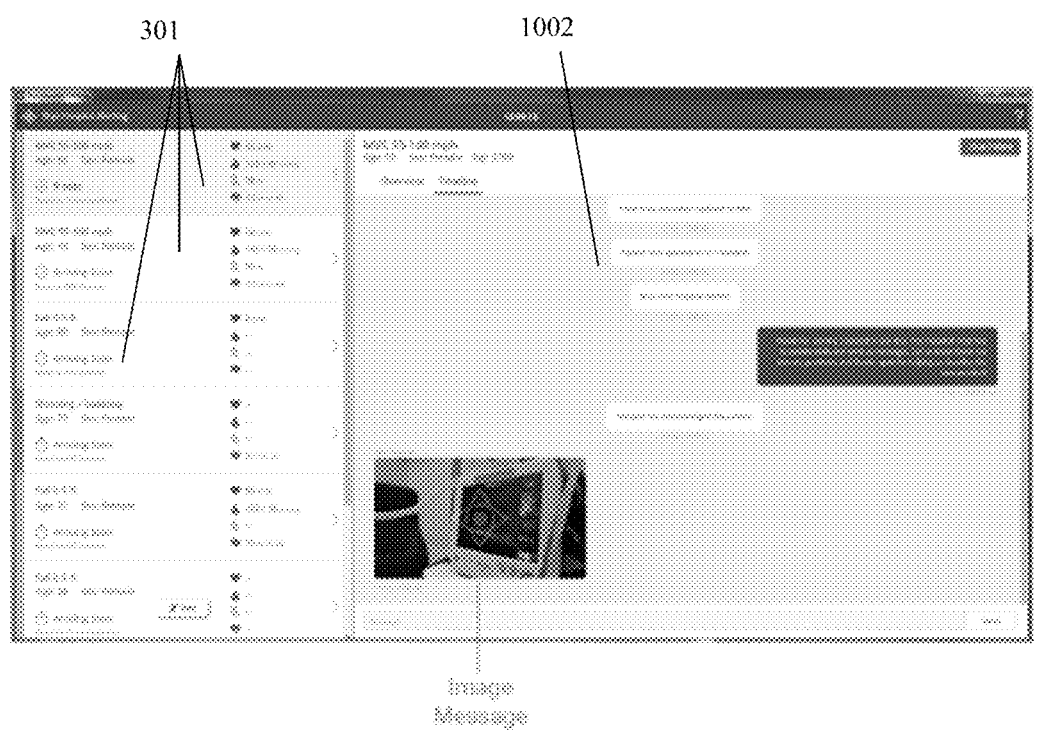
FIG. 16 is an exemplary patient timeline suitable for performing exemplary embodiments of the present disclosure.

The mobile devices of EMS or other first responders can have a built in GPS that calculates the location of the mobile device. Embodiments provide that a map can be provided to hospital staff via the application or mobile device as shown in FIG. 6. Assuming the mobile device is with the EMS, the application or mobile device will be able to transmit to the hospital or trauma center to which they are driving an ETA of the patient. Since the location of the patient and the medical information of the patient will be automatically sent to the hospital that will treat the patient, there is no longer a need to verbally transmit or speak with the hospital staff. This reduces the likelihood of lost or uncommunicated data.

Figure 4:
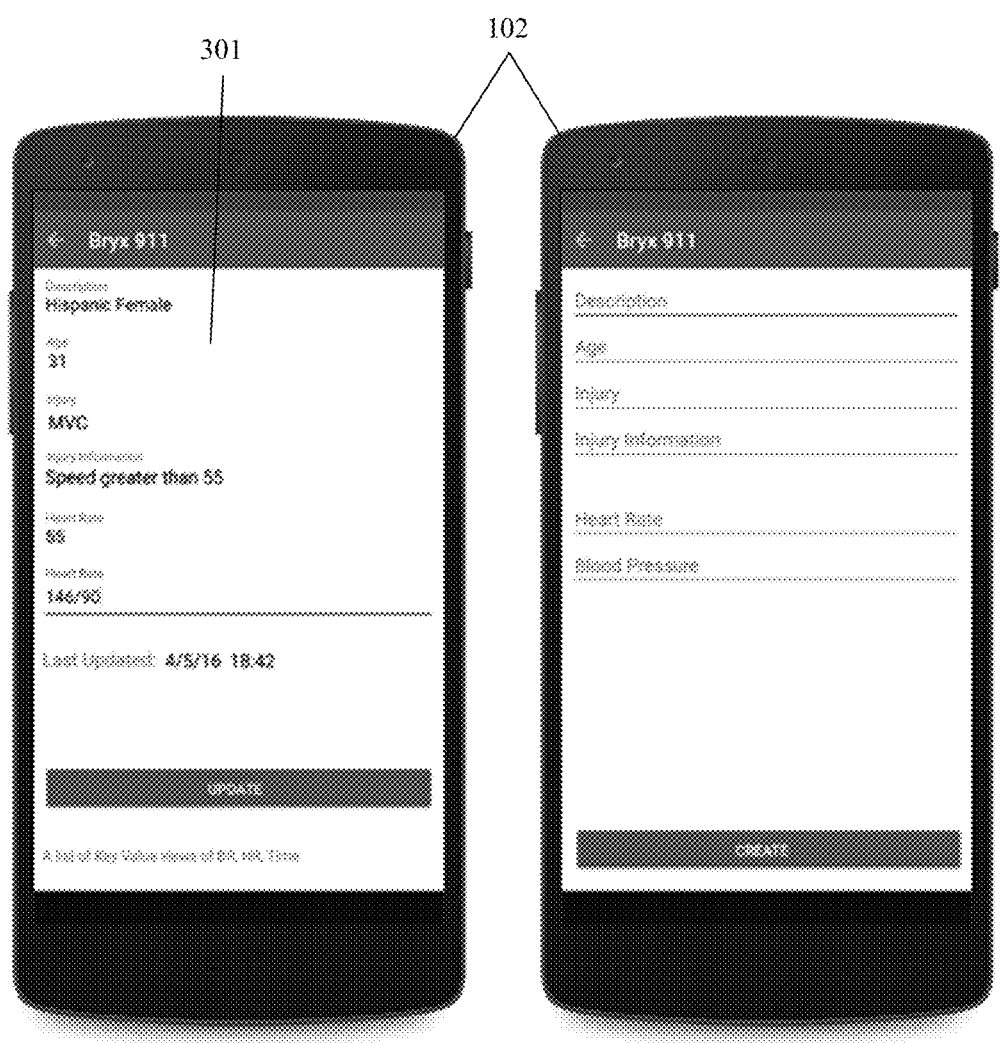
FIG. 4 illustrates some of the exemplary information that can be entered in embodiments of application of the present disclosure.
Figure 5:
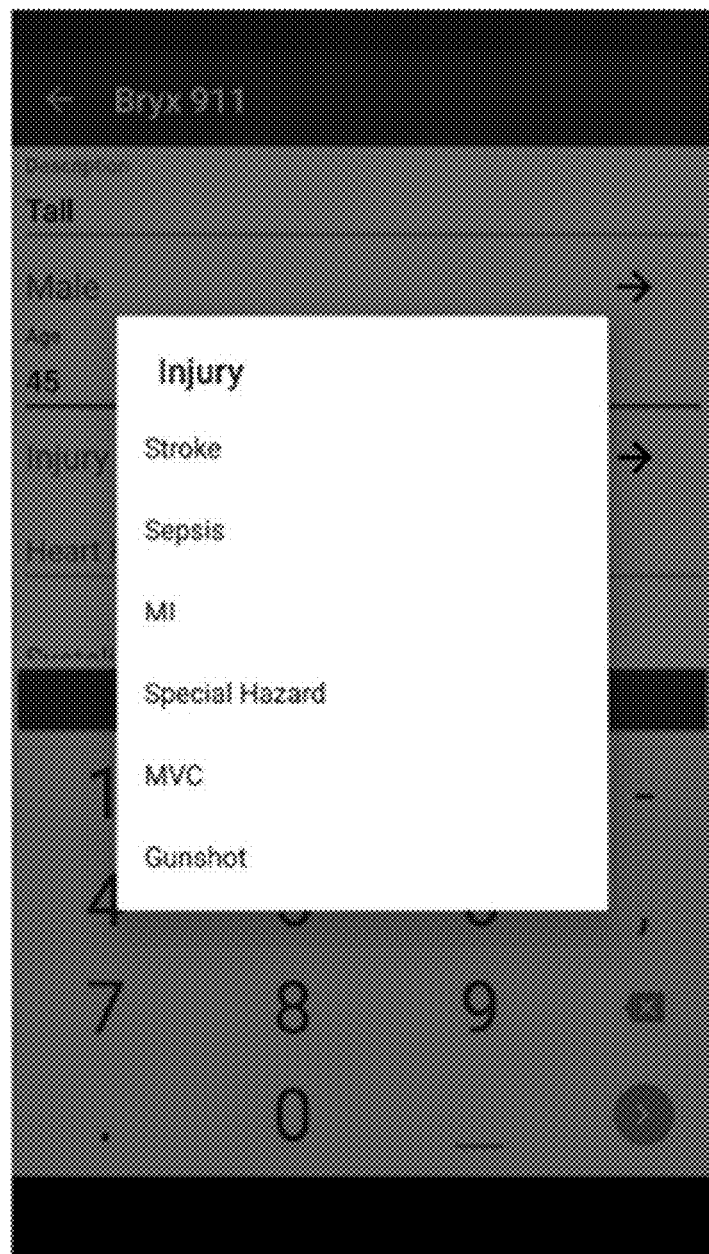
FIG. 5 illustrates an exemplary display for entering patient injury information in an exemplary application of the present disclosure.

Referring to FIGS. 3, 4, 8, 8a, 9, 10, and 11, depicted is an exemplary mobile device with the medical information available to EMS or hospital staff. Shown in FIG. 4 are a list of possible patients that can be selected in order to view their medical information. Once a specific patient is selected, the basic medical information obtained by EMS is provided, which can include the age, race, reason for the injury/medical emergency, the patient's heart rate, and blood pressure. It should be understood that additional medical information can be added to this list if it is pertinent to the treatment of the patient. Provided also is the ability to send the alert to hospital staff via the "SEND ALERT" button. In FIG. 4, depicted is an exemplary update of an existing patient information screen and a blank screen for inputting information for a new patient.

Embodiments of the present disclosure provide an application on a mobile device operable to provide alerts and up to date information to a hospital or trauma center to which a patient is going or being taken prior to their arrival. FIGS. 3-16 illustrate embodiments of an exemplary application and its functionality. Embodiments allow a new patient to be added to a particular job or emergency situation by first responders. The patient along with their medical and emergency information are available to any user of the application whether it be first responders or hospital staff. Once a user (e.g., first responder or hospital staff) views a patient from a job or emergency situation, that user will receive notifications on their mobile device when that patient's information is updated. The user will also be able to receive an alert on their mobile device of any update in the patient's vital information that is updated by first responders or emergency equipment (e.g., blood pressure, blood oxygen, or heart rate monitors) in the application. Embodiments further provide that a user (e.g., first responder entering patient information or hospital staff) will be notified through the application whether patient information and updates to patient information have been viewed/received by hospital staff.

Embodiments provide that patient information and patient profile including updates to patient information from an emergency will be maintained with the patient information within a patient timeline 1002 (shown in FIGS. 10, 11, 15, 16). The patient timeline 1002 will include a running list of patient information, updates to patient information and messaging between different users of the application (shown in FIG. 11). For instance, embodiments of the patient timeline 1002 allow a user to electronically send or post a message 1004 to the patient timeline 1002, which can be viewed and responded to by other users (e.g., first responders and hospital staff). Embodiments of the patient timeline further allow users to send/post information from their mobile device or other electronic device (e.g., photos, images, text, voice files, video files, etc.) to the patient timeline 1002. Embodiments also allow a user to view, check, or verify whether other users have accessed or viewed patient information that is accessible on the patient timeline.

Embodiments provide a map and patient list (shown in FIGS. 12 and 14) can be accessed by a user's mobile device or other electronic device or by a trauma center via the application. The map 1202 is operable to depict a list of patients and profiles 301 along with their medical information, ETA to a hospital/trauma center 1204, and their most-recent vital information/entries from the patient timeline. The map 1202 also displays each patient's current location 1206. The patient list can contain active patients that have been alerted to the hospital or other trauma center along with pertinent medical information. The patient list can include color indications of the severity of their medical condition and can be arranged in the order in which they will arrive to the hospital or trauma center.

Embodiments of the present disclosure also provide that on-board diagnostic (OBD) information from an automobile, car, or truck (or any mode of transportation including bus, helicopter, or van) can be obtained from the automobile, and transmitted to EMS mobile devices and hospital or trauma center personnel. Automobiles often have on-board diagnostic and reporting capabilities known as OBD 138. The OBD 138 records and maintains information related to the speed of the automobile 140, the engine, RPM, fuel efficiency and other sensor data including direction of impact for an accident and whether the airbags were deployed.

Embodiments of the present disclosure provide a mobile device or application that can obtain the information from an automobiles 140 OBD 138 (including car, truck, bus, helicopter, or van) and transmit the information to EMS and/or hospital staff (e.g., to be included in a trauma level assessment or to be added to the patient profile 301). In one embodiment, a device (e.g., emergency responder UE 102) can be operably attached to an automobile 138. The device is operable to communicate with the automobiles 138 OBD 140 such that after an accident or other emergency situation, the device can transmit the OBD data to any of the elements shown in FIG. 1 including an EMS mobile device. The information sent to the EMS mobile device or application can include crash data, accelerometer data, direction of travel, and impact forces where applicable. In another instance, a driver can download an application to their mobile device. The application, using the mobile device's onboard accelerometer and GPS will record recent data. When there is a crash, the accelerometer will be able measure the change in momentum above a certain threshold to "know" that there has been an accident. Some of the other information, how many impacts occurred, the G-force of the impact, and the mechanism of injury. The application will then operably transmit the accelerometer and GPS data to EMS and hospital personnel after the accident.

In another instance, EMS personnel would be able to obtain the crash data from the driver's mobile device when they arrive at the scene of the accident or are within a certain radius. In this embodiment, a driver's mobile device (e.g., smartphone, tablet, wearable device, computer, etc.) is operable to communicate (e.g., via Wi-Fi, Bluetooth, etc.) with the driver's vehicle such that the mobile device can receive data from the vehicle related to the vehicle's crash data, accelerometer data, direction of travel, and impact forces. The driver's mobile device will then be operable to transmit the vehicle crash information to server and to emergency responders.

Embodiments of the present disclosure further provide that emergency information can be obtained by UAVs or drones that on at the emergency location. The information from the UAVs (e.g., photos, videos, infrared pictures, gas and air quality data) can be transmitted to EMS mobile devices and then to the appropriate hospital or trauma center staff.

Reference is now made to FIG. 17, which presents a logic flow diagram that illustrates a method, apparatus, and computer-readable medium for performing exemplary embodiments of this disclosure. Block 1702 presents (a) receiving, by a processor, a first data, the first data related to medical information of an individual; (b) receiving, by a processor, a plurality of second data, the plurality of second data from a plurality of devices with information of the individual; (c) determining, by the processor, a trauma level of the individual based on the received first data and the received plurality of second data; and (d) transmitting, by the processor, the first data and the plurality of second data to a trauma center. Block 1704 the specifies the method further comprising sending an alert with the first data and the plurality of second data to a trauma center.

The diagram continues at block 1706 which states wherein the first data includes medical information from a first responder. Block 1708 then states wherein the second data includes medical information from at least one of a heart rate monitor, a blood pressure measuring device, an automobile OBD, an IV, an oxygen level measuring device, and a thermometer. Next at block 1710 relates to wherein the trauma center is a set of trauma center personnel able to respond to the trauma level. Then block 1712 indicates wherein the trauma center is a hospital. Block 1714 relates to wherein the transmitting includes an alert and an estimated time of arrival. Finally block 1716 specifies wherein determining a trauma level includes determining a medical treatment for the individual.

Referring now to FIG. 18 is another logic flow diagram that illustrates another method, apparatus, and computer-readable medium for performing exemplary embodiments of this disclosure. Block 1802 presents (a) receiving, by a processor, a first data, the first data related to medical information of an individual; (b) receiving, by a processor, a plurality of second data, the plurality of second data from a plurality of devices with medical information of the individual; (c) determining, by the processor, (i) a profile based on the first data and the plurality of second data, and (ii) which subset of a plurality of user equipments require the profile, and (d) transmitting, by the processor, the profile to the subset of the plurality of user equipments. Next block 1804 indicates wherein the determining which subset of the plurality of user equipments require the profile is based on a location of the individual and an expertise of the user of the subset of the plurality of the user equipments.

Following block 1804, block 1806 states wherein a trauma center to which the individual will be transported is part of the subset of the plurality of user equipments. Then 1808 relates to wherein the first data comprises at least one of injury information, heart rate, blood pressure, an oxygen level, and temperature. 1810 states wherein the second data includes medical information from at least one of a heart rate monitor, a blood pressure measuring device, an automobile OBD, an IV, an oxygen level measuring device, and a thermometer. 1812 relates to wherein the transmitting includes an alert and an estimated time of arrival.

The logic flow diagrams of FIG. 17 and FIG. 18 may be considered to illustrate the operation of a method, and a result of execution of computer program instructions stored in a computer-readable memory, and a specific manner in which components of an electronic device are configured to cause that electronic device to operate, whether such an electronic device is a smartphone, application, user equipment, server, computer, laptop, or trauma center computer system, or one or more components thereof. The various blocks shown in FIG. 17 and FIG. 18 may also be considered as a plurality of coupled logic circuit elements constructed to carry out the associated function(s), or specific result of strings of computer program instructions or code stored in a memory.

Various embodiments of the computer-readable medium or computer-readable memory include any data storage technology type which is suitable to the local technical environment, including but not limited to semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. Various embodiments of the processor include, but are not limited to general purpose computers, special purpose computers, microprocessors, digital signal processors and multi-core processors.

This disclosure has been described in detail with particular reference to the above described embodiments, but it will be understood that variations and modifications can be effected within the spirit and scope of this disclosure. The presently disclosed embodiments are therefore considered in all respects to be illustrative and not restrictive. The scope of the invention is indicated by the appended claims, and all changes that come within the meaning and range of equivalents thereof are intended to be embraced herein.

The invention claimed is:

1. A method of aiding emergency response, the method comprising:
   (a) receiving, by a processor, emergency information corresponding to an individual from an emergency services dispatcher;
   (b) receiving, by the processor, a first data, the first data related to medical information of the individual;
   (c) receiving, by the processor, a plurality of second data, the plurality of second data from a plurality of devices with information of the individual;
   (d) determining, by the processor, a trauma level of the individual based on the received first data, the emergency information and the received plurality of second data;
   (e) determining, by the processor, at least one trauma center personnel able to respond to the determined trauma level; and
   (f) transmitting, by the processor, the first data, the emergency information and the plurality of second data to the at least one trauma center personnel and a trauma center.

2. The method according to claim 1, the method further comprising sending an alert with the first data and the plurality of second data to a trauma center.

3. The method according to claim 1, wherein the first data includes medical information from a first responder.

4. The method according to claim 1, wherein the second data includes medical information from at least one of a heart rate monitor, a blood pressure measuring device, an automobile OBD, an IV, an oxygen level measuring device, and a thermometer.

5. The method according to claim 1, wherein the trauma center is a set of trauma center personnel able to respond to the trauma level.

6. The method according to claim 1, wherein the trauma center is a hospital.

7. The method according to claim 1, wherein the transmitting includes an alert and an estimated time of arrival.

8. The method according to claim 1, wherein determining a trauma level includes determining a medical treatment for the individual.

9. An apparatus comprising at least one processor and a memory storing computer program instructions executable by the at least one processor, wherein the memory and the computer program instructions and the processor are configured to cause the apparatus to at least:
   (a) receive emergency information corresponding to an individual from an emergency services dispatcher;
   (b) receive a first data, the first data related to medical information of the individual;
   (c) receive a plurality of second data, the plurality of second data from a plurality of devices with information of the individual;
   (d) determine a trauma level of the individual based on the received first data, the emergency information and the received plurality of second data;
   (e) determine at least one trauma center personnel able to respond to the determined trauma level; and
   (f) transmit the first data, the emergency information and the plurality of second data to a trauma center and the at least one trauma center personnel.

10. The apparatus according to claim 9, the memory and the computer program instructions and the processor are configured to cause the apparatus to send an alert with the first data and the plurality of second data to a trauma center.

11. The apparatus according to claim 9, wherein the first data includes medical information from a first responder.

12. The apparatus according to claim 9, wherein the second data includes medical information from at least one of a heart rate monitor, a blood pressure measuring device, an automobile OBD, an IV, an oxygen level measuring device, and a thermometer.

13. The apparatus according to claim 9, wherein the transmitting includes an alert and an estimated time of arrival.

14. The apparatus according to claim 9, wherein determining a trauma level includes determining a medical treatment for the individual.

15. A method for aiding emergency response, the method comprising:
(a) receiving, by a processor, emergency information corresponding to an individual from an emergency services dispatcher;
(b) receiving, by the processor, a first data, the first data related to medical information of the individual;
(c) receiving, by the processor, a plurality of second data, the plurality of second data from a plurality of devices with medical information of the individual;
(d) determining, by the processor, (i) a profile based on the first data, the emergency information and the plurality of second data, and (ii) which subset of a plurality of user equipments require the profile, and
(e) transmitting, by the processor, the profile to the subset of the plurality of user equipments, wherein the plurality of user equipments are all user equipments of a trauma center personnel, and wherein the subset of the plurality of user equipments are user equipments of trauma center personnel able to respond to the determined profile.

16. The method according to claim 15, wherein the determining which subset of the plurality of user equipments require the profile is based on a location of the individual and an expertise of the user of the subset of the plurality of the user equipments.

17. The method according to claim 15, wherein a trauma center to which the individual will be transported is part of the subset of the plurality of user equipments.

18. The method according to claim 15, wherein the first data comprises at least one of injury information, heart rate, blood pressure, an oxygen level, and temperature.

19. The method according to claim 15, wherein the second data includes medical information from at least one of a heart rate monitor, a blood pressure measuring device, an automobile OBD, an IV, an oxygen level measuring device, and a thermometer.

20. The method according to claim 15, wherein the transmitting includes an alert and an estimated time of arrival.

* * * * *